US011386977B2

(12) United States Patent
Lemmer et al.

(10) Patent No.: US 11,386,977 B2
(45) Date of Patent: Jul. 12, 2022

(54) ENHANCED AMPLICON SEQUENCING ANALYSIS

(71) Applicants: Translational Genomics Research Institute, Phoenix, AZ (US); Arizona Board of Regents, Acting for and on Behalf of Northern Arizona University, Flagstaff, AZ (US)

(72) Inventors: Darrin Lemmer, Flagstaff, AZ (US); Jolene Bowers, Flagstaff, AZ (US); Erin Kelley, Flagstaff, AZ (US); David Engelthaler, Flagstaff, AZ (US); Elizabeth Driebe, Flagstaff, AZ (US); Paul Keim, Flagstaff, AZ (US)

(73) Assignees: The Translational Genomics Research Institute, Flagstaff, AZ (US); Arizona Board of Regents for and on behalf of Northern Arizona University, Flagstaff, AZ (US)

( * ) Notice: Subject to any disclaimer, the term of this patent is extended or adjusted under 35 U.S.C. 154(b) by 1023 days.

(21) Appl. No.: 15/576,495

(22) PCT Filed: May 23, 2016

(86) PCT No.: PCT/US2016/033810
§ 371 (c)(1),
(2) Date: Nov. 22, 2017

(87) PCT Pub. No.: WO2016/191384
PCT Pub. Date: Dec. 11, 2016

(65) Prior Publication Data
US 2018/0173843 A1   Jun. 21, 2018

Related U.S. Application Data

(60) Provisional application No. 62/165,612, filed on May 22, 2015.

(51) Int. Cl.
| | |
|---|---|
| G01N 33/48 | (2006.01) |
| G16B 30/00 | (2019.01) |
| G16B 20/00 | (2019.01) |
| G16B 20/20 | (2019.01) |
| G06G 7/58 | (2006.01) |

(52) U.S. Cl.
CPC ............. *G16B 30/00* (2019.02); *G16B 20/00* (2019.02); *G16B 20/20* (2019.02)

(58) Field of Classification Search
None
See application file for complete search history.

(56) References Cited

U.S. PATENT DOCUMENTS

2014/0249037 A1   9/2014   Fry et al.

OTHER PUBLICATIONS

Colman, R. E., et al. Detection of Low-Level Mixed-Population Drug Resistance in *Mycobacterium tuberculosis* Using High Fidelity Amplicon Sequencing. PLoS One 2015; 10(5):e0126626; XP055303074, DOI: 10.1371/journal.pone.0126626, 18 pages.
Colman, R. E., et al. Detection of Low-Level Mixed-Population Drug Resistance in *Mycobacterium tuberculosis* Using High Fidelity Amplicon Sequencing—Online supplementary material: Table S5. PLoS One 2015; XP055303576, Retrieved from the Internet: URL:http://journals.plos.org/plosone/article?id=10.1371/journal.pone.0126626#sec017 [retrieved on Sep. 19, 2016], 1 page.
Inouye,M., et al. SRST2: Rapid Genomic Surveillance for Public Health and Hospital Microbiology Labs. Genome Medicine 2014; 6(11):90, 16 pages.
Giongo, A., et al. PANGEA: Pipeline for Analysis of next Generation Amplicons. The ISME Journal 2010; 4(7):852-861, 10 pages.
Bradley, P., et al. Rapid antibiotic resistance predictions from genome sequence data for *Staphylococcus aureus* and *Mycobacterium tuberculosis*. Nat Commun 2015; 6:10063, 15 pages.

*Primary Examiner* — Eric S Dejong

(57) ABSTRACT

An Amplicon Sequencing Analysis Pipeline (ASAP) system (120, 600) characterizes a genetic sample. The ASAP system (120, 600) receives assay configuration data individually associating reference sequences and genetic characteristics. The ASAP system (120, 600) processes amplicon sequencing data and the reference sequences to characterize the genetic sample based on the individual associations between the reference sequences and the genetic characteristics in the assay configuration data. The ASAP (120, 600) system transfers genetic data indicating the genetic characteristics for the genetic sample and indicating interpretation metrics for amplicon sequencing read depth and quality related to the genetic characteristics.

6 Claims, 6 Drawing Sheets

```
{
  "Assay" : [
    {
      "name" : "Assay 1",
      "type" : "presence/absence",
      "Target" : {
        "function" : "strain ID",
        "gene_name" : "E. coli",
        "start_position" : 5,
        "end_position" : 17,
        "reverse_comp" : FALSE
        "Amplicon" : [
          {
            "variant_name" : "E. coli x",
            "sequence" : "AGTCAATCATGCC",
         "Significance" : {
             "message" : "E. coli strain x present"
             }
             },
        OR
            {
          "variant_name" : "E. coli y",
             "sequence" : "AGTCAATCATGCG",
          "Significance" : {
            "message" : "E. coli strain y absent"
            }
           }]
         }
      }]
}
```

FIGURE 4

GENETIC DATA STRUCTURE 500

| Sample | Target | # Reads | Target Significance | Target Type | SNPs Found |
|---|---|---|---|---|---|
| UR-058 | Ec_M1_UT | 5107 | Species ID: Escherichia coli | Presence/absence | |
| | Kp_M1_UT1nv | 11092 | Species ID: Klebsiella pneumoniae | Presence/absence | |
| | ST239_UT1 | 1 | | | |
| | Sa_M2_UT1 | 1 | | | |
| | VISA_rpoB481_UT1 | 2 | | | |
| | ascA_UT1 | 26 | | | |
| | blaZ_UT1 | 2 | | | |
| | ermC_UT1 | 24 | | | |
| | gyrA_ACBA_UT1 | 2 | | | |
| | gyrA_Ecoli_UT1 | 4208 | Fluoroquinolone resistance | SNP based | None |
| | gyrA_Kleb_UT1 | 38178 | Fluoroquinolone resistance | SNP based | 45:A->T |
| | gyrA_staph_UT1 | 1 | | | |
| | mecA_UT1 | 3 | | | |
| | parC_Ecoli_UT1 | 1920 | Fluoroquinolone resistance | SNP based | None |
| | parC_Kleb_UT1 | 9323 | Fluoroquinolone resistance | SNP based | 27:G->C |
| | parC_staph_UT1 | 3 | | | |
| | tetK_UT1 | 6 | | | |
| | tetM_UT1 | 6626 | Tetracycline resistance | Presence/absence | |

FIGURE 5

ENHANCED AMPLICON SEQUENCING ANALYSIS

RELATED APPLICATIONS

This application claims the benefit of PCT Patent Application Serial No. PCT/US2016/033810 filed on May 23, 2016, and entitled "ENHANCED AMPLICON SEQUENCING ANALYSIS," which claims the benefit of and priority to U.S. Provisional Application Ser. No. 62/165,612, filed on May 22, 2015, and entitled "SYSTEMS AND METHODS FOR AMPLICON SEQUENCING ANALYSIS," both of which are hereby incorporated by reference in their entirety.

This invention was made with Government support under RO1 A1090782 awarded by the National Institutes of Health. The Government has certain rights in the invention.

TECHNICAL BACKGROUND

Deoxyribonucleic Acid (DNA) is made of nucleotides that are typically arranged in a double helix of sequential base pairs. DNA sequencers process a sample like soil and tissue to characterize the genetic content of the sample. The sequencing data from the DNA sequencers is often used for medical and biological research. For example, the DNA sequencing data from human and animal tissue is often used for cancer treatment. In another example, the DNA sequencing data from soil and waste may be used to research bacterial species like *Escherichia coli* and *Klebsiella pneumoniae*.

Various DNA sequencers and sequencing techniques are available that produce prodigious amounts of sequencing data. These giant data products are further complicated by a variety of different data formats and biological information represented by the data.

DNA sequencing copies (amplifies) relatively small portions of the DNA across various regions in a genetic sample. A large number of DNA copies (amplicons) are often generated for target regions in the genetic material. The DNA sequencer then reads these amplicons to generate sequencing data Amplicon read depth refers to the number of amplicons with the same nucleotide pattern from the same genome location. For example, *E. coli* has multiple DNA variants, the read depth for one of the variants is the number of amplicons that correspond to the reference sequence for that DNA variant.

Sequencing data may be interpreted to characterize the genetic content in a sample. For example, *K. pneumoniae* DNA may be processed to characterize various regions of the bacterial genome at differing read depths. The sequencing data is further processed to characterize details like Single Nucleotide Polymorphisms (SNPs) for antibiotic resistance.

To identify a SNP, the amplicon sequencing analysis pipeline compares the sequencing data to a reference sequence in an alignment process. Reference sequences may come in various lengths relative to the sequencing data from the sample. The amount of overlap between the amplicon sequencing data and the reference sequence is referred to as amplicon coverage. The ratio of identity between the amplicon sequencing data and the reference sequence is referred to as amplicon identity. High amplicon coverage and high amplicon identity are desired when matching DNA sequence data to a DNA reference sequence.

Unfortunately, medical and biological research using DNA sequencing is a complex process. The ability to run different assays with various functions and multiple reference sequences creates even more complexity. In addition, interpreting the resulting output is cumbersome.

TECHNICAL OVERVIEW

An Amplicon Sequencing Analysis Pipeline (ASAP) system characterizes a genetic sample. The ASAP system receives assay configuration data individually associating reference sequences and genetic characteristics. The ASAP system processes amplicon sequencing data and the reference sequences to characterize the genetic sample based on the individual associations between the reference sequences and the genetic characteristics in the assay configuration data. The ASAP system transfers genetic data indicating the genetic characteristics for the sample and indicating interpretation metrics for the genetic characteristics. The interpretation metrics may indicate sequencing depth and quality for individual genetic characteristics. For a complex target assay, the interpretation metrics are rendered to easily associate select sequencing metrics and quality data with the individual genetic characteristics that comprise the target assay.

DESCRIPTION OF THE DRAWINGS

FIG. 4 illustrates an example of a JavaScript Object Notation (JSON) file to input assay configuration data.

FIG. 5 illustrates an example of the output from the ASAP system.

TECHNICAL DESCRIPTION

Figure 1:
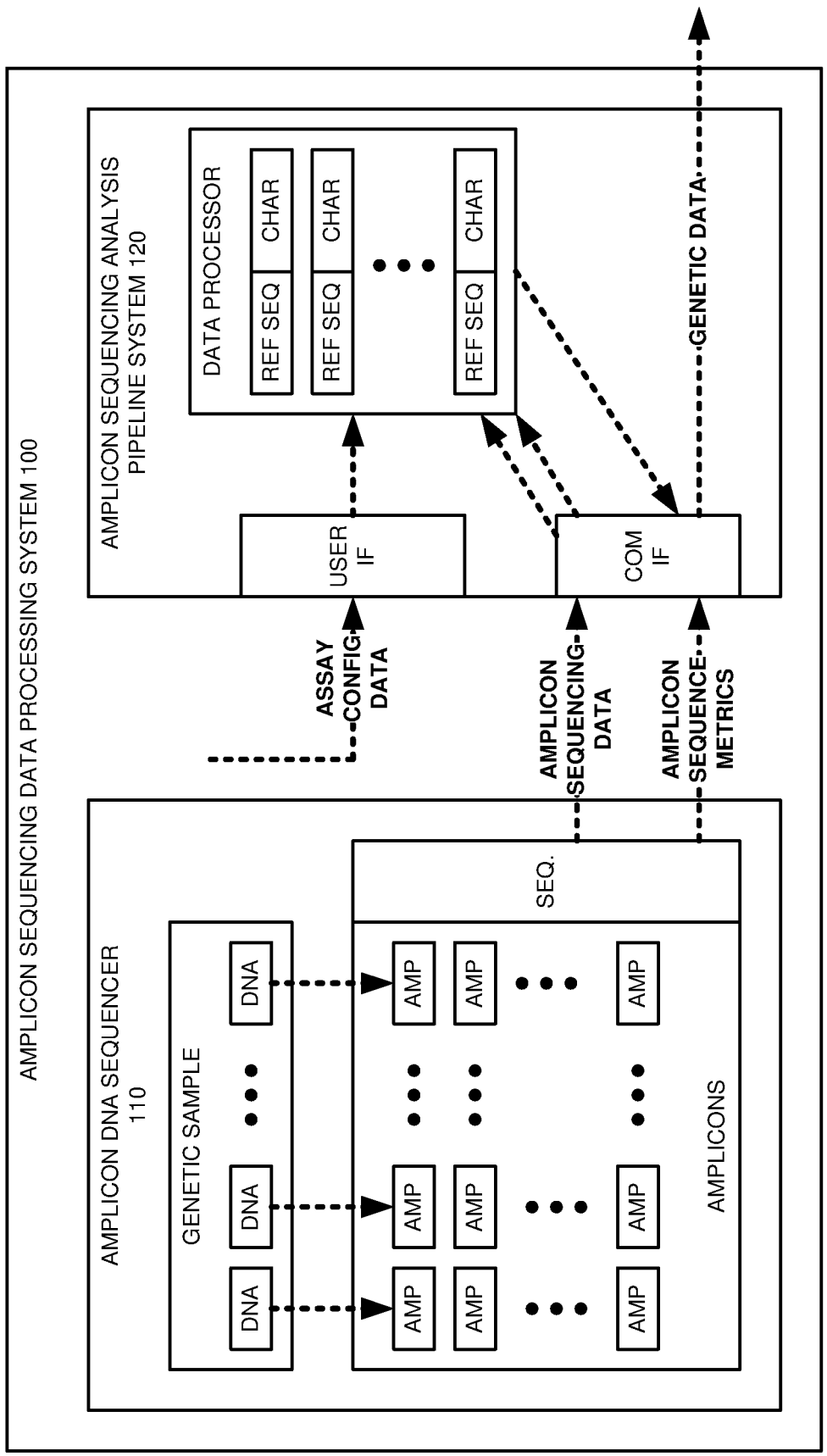
FIGS. 1-2 illustrate an enhanced amplicon sequencing data processing system to identify genetic characteristics and indicate interpretation metrics for the genetic characteristics.

FIG. 1 illustrates amplicon sequencing data processing system 100 to identify genetic characteristics of a sample and indicate interpretation metrics for the genetic characteristics Amplicon sequencing data processing system 100 comprises amplicon DNA sequencer 110 and Amplicon Sequencing Analysis Pipeline (ASAP) system 120. If desired, the components of amplicon DNA sequencer 110 could be integrated into ASAP system 120.

Amplicon sequencer 110 amplifies the DNA in a sample to generate amplicons (AMP on the figure) of the DNA Amplicon sequencer 110 then reads the amplicons to generate amplicon sequencing data and amplicon sequencing metrics. The amplicon sequencing data describes the nucleotide arrangements. The amplicon sequencing metrics describe the amplicon sequencing operation with data like read confidence factors.

ASAP system 120 receives assay configuration data into its user interface. The assay configuration data individually associates reference sequences (REF SEQ on the figure) and genetic characteristics (CHAR on the figure). For example, assay requirements may be loaded into a data template that the data processor translates into a JavaScript Object Notation (JSON) file for alignment and interpretation. The data processor then executes the JSON file to drive a target assay. For a complex target assay, the JSON file may include individual genetic characteristics, their logical operators (AND/OR/NOT), significance data, and assay thresholds and other requirements.

Exemplary genetic characteristics include species identity, species variant, antibiotic resistance, virulence factor, species strain, haploid type, and Single Nucleotide Polymorphisms (SNPs). Interpretation metrics sequencing read depth and quality. Exemplary interpretation metrics include the number of mapped/unmapped reads, number of aligning reads, breadth of coverage, consensus sequence, depth of coverage at each position, consensus proportion at each position, average depth of coverage, SNP position, SNP depth of coverage, amount of reference and SNP calls, number/percentage of reads containing SNPs, full base distribution at position, significance of SNP, SNP Region of Interest (ROI), number of reads aligning to ROI, reference sequence of ROI, most prevalent nucleotide sequence at ROI, number/percentage of reads containing the prevalent sequence, and amino acid and nucleotide sequence distributions.

ASAP system 120 compares the amplicon sequencing data to the reference sequence(s) to identify genetic characteristics based on the individual associations in the assay configuration data. ASAP system 120 generates interpretation metrics like read depth for the various genetic characteristics. ASAP system 120 may also generate other interpretation metrics like the amplicon breadth of coverage and the amplicon identity for specific genetic characteristics. For a complex assay, ASAP system 120 generates interpretation metrics to readily assess the amplicon sequencing depth and quality of the assay.

ASAP system 120 drives its communication interface to transfer genetic data with the genetic characteristics and related interpretation metrics like confidence, read depth, amplicon coverage, and amplicon identity for the individual genetic characteristics. The genetic data may be graphically presented in custom spreadsheets. Thus, medical and biological researchers may use the genetic data to easily analyze the significance and accuracy of their amplicon-based assays.

The assay configuration data drives ASAP system to perform pipeline analysis. The assay configuration data specifies the interpretation of sequencing metrics like read depth and confidence. The assay configuration data may further specify amplicon identity thresholds for the reference sequences. ASAP system 120 uses the amplicon identity thresholds to determine amplicon identity between the amplicon sequencing data and the reference sequences. The genetic data indicates these amplicon identity thresholds for individual genetic characteristics like antibiotic resistance and virulence factor.

The assay configuration data may be configured as a JSON file that specifies an assay type, various target function(s), multiple reference sequences, significance, and interpretation metrics. The input JSON may optionally specify SNPs and ROIs. Some examples of assay types include presence/absence, SNP, gene variant, and ROI. A user may also define target functions, such as species ID, strain ID, antibiotic resistance type, and/or virulence factor detection. The following JSON template is provided for illustrative purposes.

```
                         JSON Template

{
    "Assay" : [
        {
            "name" : "string",
            "type" : "presence/absence | SNP | gene variant |
region of interest | mixed",
            "Target" : {
                "function" : "species ID | strain ID | resistance type |
virulence factor",
                "gene_name" : "string",
                "start_position" : int,
                "end_position" : int,
                "reverse_comp" : boolean
                "Amplicon" : [
                    {
                        "variant_name" : "string",
                        "sequence" : "string",
                        "SNP" : [
                            {
                                "position" : "int | 'any'",
                                "reference" : "char",
                                "variant" : "char",
                                "name" : "string",
                                "Significance" :
                                    {
                                        "message" : "string"
                                    }
                            }
                        ],
                        "RegionOfInterest" : [
                            {
                                "positions" : "string",
                                "aa_sequence" : "string",
                                "nt_sequence" : "string",
                                "mutations" : "string",
                                "name" : "string",
                                "Significance" :
                                    {
                                        "message" : "string"
                                    }
                            }
                        ],
                        "Significance" :
                            {
                                "message" : "string"
                            }
                    }
                ],
            }
        }
    ]
}
```

Figure 2:
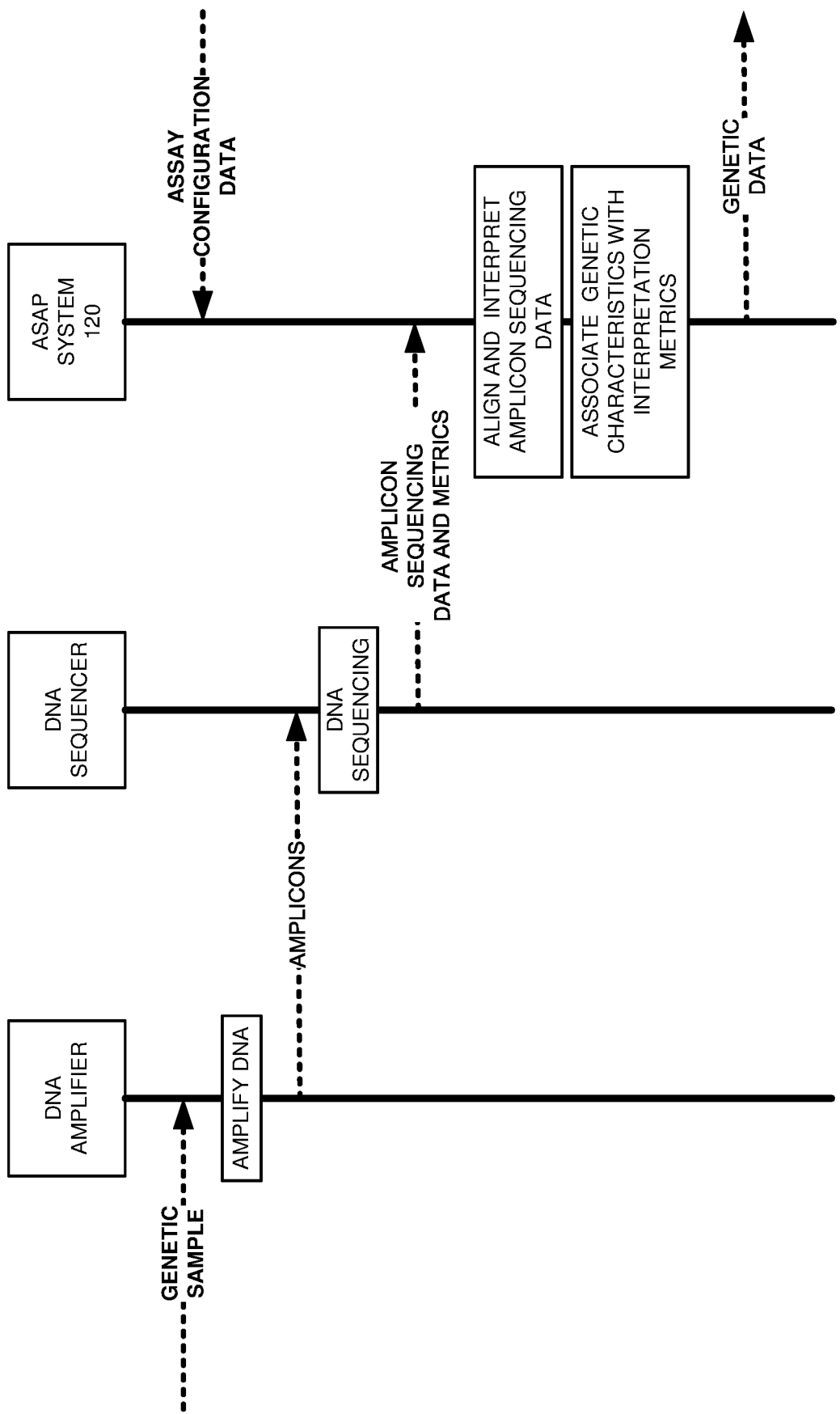

FIG. 2 illustrates the operation of amplicon sequencing data processing system 100 to identify genetic characteristics and indicate interpretation metrics for the genetic characteristics. A DNA amplifier in amplicon sequencer 110 amplifies the DNA in a genetic sample to generate amplicons. The DNA amplifier transfers the amplicons to the DNA sequencer. The DNA sequencer reads the amplicons to generate amplicon sequencing data and amplicon sequencing metrics. The amplicon sequencing data describes the nucleotide arrangement of the genetic material. The amplicon sequencing metrics describe operational data like read confidence and amplicon size.

ASAP system 120 receives assay configuration data that individually associates reference sequences and genetic characteristics. The assay configuration data may specify interpretation metrics like amplicon identity and/or coverage on an individual genetic characteristic basis. For example, the assay configuration data may specify an amplicon identity to determine a specific strain of *E. coli* and another amplicon identity to associate antibiotic resistance with that *E. coli* strain. Thus, a researcher can perform a complex target assay. The interpretation metrics may indicate sequencing depth and quality for individual genetic characteristics. For complex target assays, the interpretation metrics are rendered to easily associate select sequencing metrics with individual characteristics that form the target assay.

ASAP system 120 aligns the amplicon sequencing data to the reference sequences and interprets the resulting matches, mismatches, additions, and omissions. ASAP system 120 associates genetic characteristics with reference sequences based on individual associations in the assay configuration data. ASAP system 120 generates interpretation metrics like read depth, amplicon coverage, and amplicon identity for individual genetic characterization(s). ASAP system 120 transfers the genetic data with the genetic characteristics and the interpretation metrics. For a complex assay, ASAP 120 may transfer assay data that correlates amplicon sequencing depth and quality with genetic characteristic of the assay.

Figure 3:
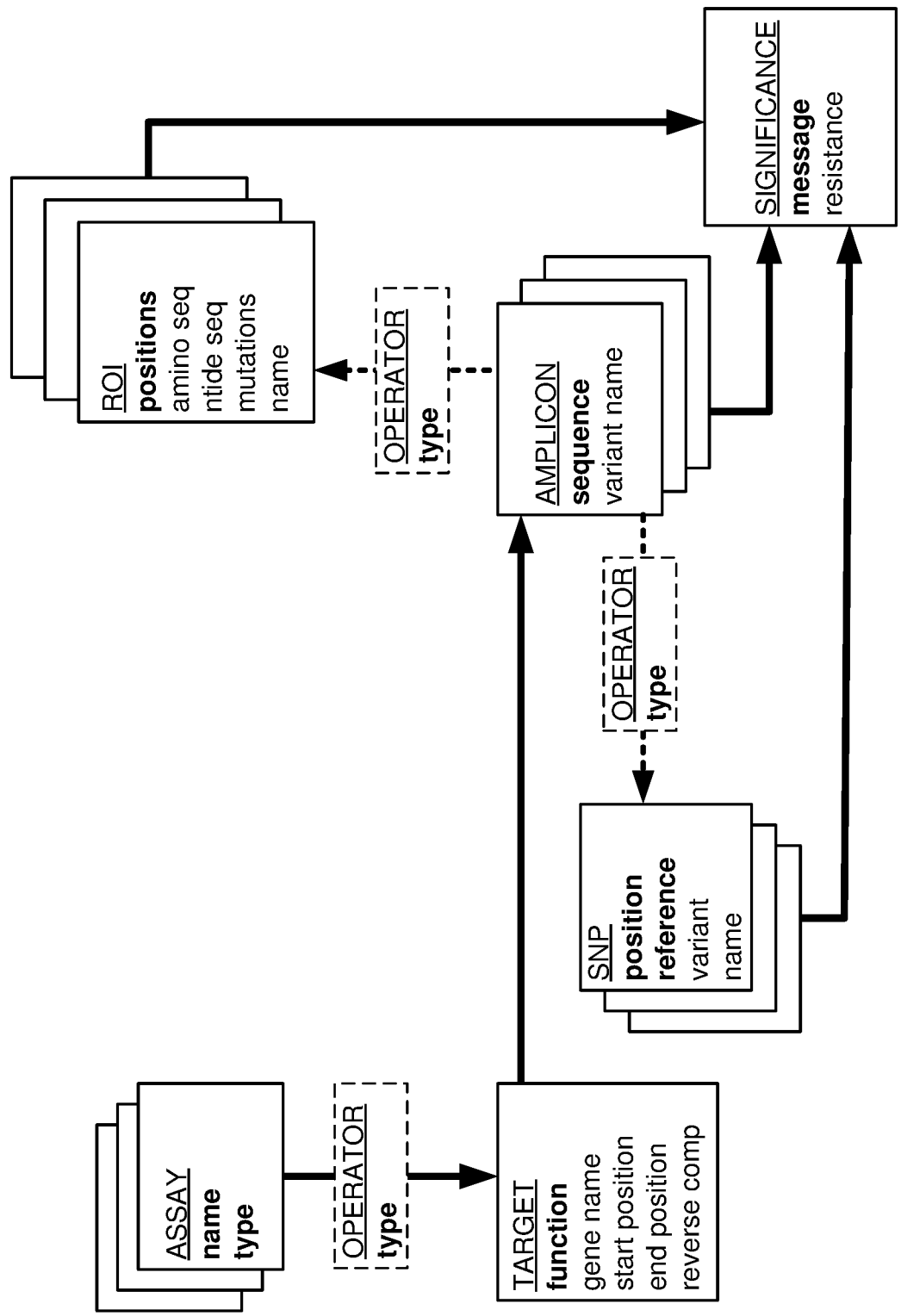
FIG. 3 illustrates an Amplicon Sequencing Analysis Pipeline (ASAP) system data architecture to identify genetic characteristics and indicate interpretation metrics for the genetic characteristics.

FIG. 3 illustrates assay configuration data for ASAP system 120, although assay configuration data may have alternate designs. The ASAP system data architecture comprises data objects and data arrays. The data objects comprise target, operator, and significance objects. The data arrays comprise assay, SNP, ROI, and amplicon arrays. A first exemplary path would be: assay→target→amplicon→significance. A second path comprises assay→target→amplicon→SNP→significance. A third path comprises: assay→target→amplicon→ROI→significance.

The operator object includes the attribute type (i.e. OR, AND, or NOT). The operator object is optional and invoked when two or more targets, SNPs, and/or ROIs are specified in the assay configuration data. The target object has the attributes: function, gene name, start position, end position, and reverse complement flag. Examples of the function attribute include species ID, strain ID, resistance type, and virulence factor. A reverse complement flag may be used to denote whether the target should be reverse complemented. The significance object has the attributes message and resistance. The message attribute indicates the message that is displayed when the conditions of the selected assay are met.

The assay array has the attributes name and type. Examples of the type attribute include presence/absence, gene variant, SNP, and ROI. The SNP array contains the attributes position, reference, variant, and name. The position attribute indicates the position of the SNP in the amplicon. The reference attribute indicates a reference character. The SNP array may be given attributes indicating whether individual SNPs are important or not important. The ROI array includes the attributes: positions, amino acid sequence (amino seq), nucleotide sequence (n tide seq), mutations, and name. The positions attribute may be specified as a range (i.e. m-n), a comma-separated list (i.e. j, k, l, and m), or a combination of the two.

The following is an example of a spreadsheet template for entering assay configuration data and provided for illustrative purposes. For a complex assay, the spreadsheet would indicate additional functions, reference sequences, operators, significance data,

| Assay Configuration Data Template | | |
|---|---|---|
| Assay | Name | Assay 1 |
|  | Type | Presence/Absence |
| Target | Function | Strain ID |
|  | Gene Name | E. coli |
|  | Start Position | 5 |

| Assay Configuration Data Template | | |
|---|---|---|
|  | End Position | 17 |
|  | Reverse Complement | Off |
| Amplicons | Reference Sequence | AGTCAATCATGCC |
|  | Variant Name | E. coli x |
|  | Significance | Presence/Absence |
|  | Reference Sequence | AGTCAATCATGCG |
|  | Variant Name | E. coli y |
|  | Significance | Presence/Absence |

FIG. 4 illustrates an exemplary example of a JSON input file, using the above assay configuration data. Assay name identifies the assay and is specified as "Assay 1." The assay type is specified as "presence/absence." The target function is specified as "strain ID." For a complex target, another function could be specified and the operator object would be invoked. The gene name is "E. coli," start position is 5, end position is 17, and the reverse complement flag is turned off. The amplicon variant names are "E. coli x," and "E. coli y." The amplicon sequences are the reference sequences used to detect the presence/absence of each variant. The significance messages indicate to the end-user whether the amplicon is present/absent. The two different amplicons are separated by an "OR" operator.

FIG. 5 illustrates genetic data structure 500 that is generated by an exemplary ASAP system. Genetic data structure 500 indicates sample ID, target, read depth, target significance, target type, and SNPs found. Genetic data structure 500 provides the biological researcher with a data summary for genetic sample.

Figure 6:
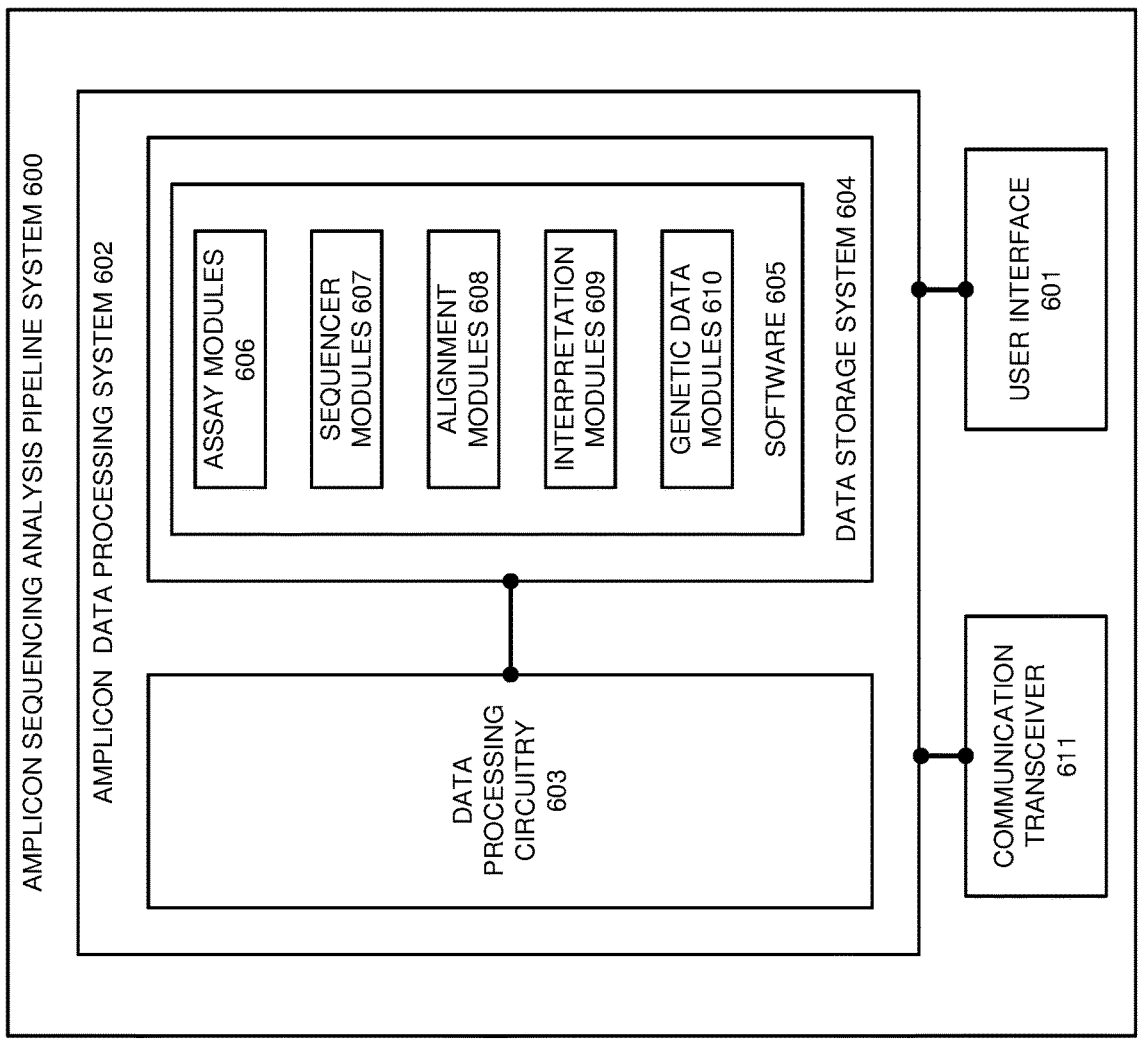
FIG. 6 illustrates an ASAP system to identify genetic characteristics and indicate interpretation metrics for the genetic characteristics.

FIG. 6 illustrates amplicon sequencing analysis pipeline system 600. Amplicon sequencing analysis pipeline 600 comprises user interface 601, amplicon data processing 602, and communication transceiver 611. Amplicon data processing system 602 includes data processing circuitry 603 and data storage system 604. Data storage system 604 stores software 605. Software 605 includes respective software modules 606-610.

Communication transceiver 611 comprises communication components, such as ports, bus interfaces, signal processors, memory, software, and the like. Data processing circuitry 603 comprises circuit boards, bus interfaces, integrated micro-circuitry, and associated electronics. Data storage system 604 comprises non-transitory, machine-readable, data storage media, such as flash drives, disc drives, memory circuitry, servers, and the like. Software 605 comprises machine-readable instructions that control the operation of processing circuitry 603 when executed. Software 605 includes software modules 606-610 and may also include operating systems, applications, data structures, utilities, and the like Amplicon sequencing analysis pipeline 600 may be centralized or distributed. All or portions of software 605 may be externally stored on one or more storage media, such as circuitry, discs, and the like. Some conventional aspects of amplicon sequencing analysis pipeline system 600 are omitted for clarity, such as power supplies, enclosures, and the like.

When executed by data processing circuitry 603, software modules 606-610 direct data processing circuitry 603 to perform the following operations. Assay modules 606 receive assay configuration data through a user interface and transfers the assay configuration data, including reference sequences, to alignment modules 608. Sequencer modules 607 receive DNA reader output signals to develop amplicon sequencing data and amplicon sequencing metrics for alignment modules 608. Alignment modules 608 position amplicon sequencing data against reference sequence(s). Interpretation modules 609 process the aligned sequence data and the assay configuration data to determine genetic characteristics and associated interpretation metrics like coverage or identity. Genetic data modules 610 format and transfer genetic data indicating genetic characteristic and associated interpretation metrics like an *E. coli* strain SNP related to its read confidence, read depth, amplicon coverage, and amplicon identity.

The above description and associated figures teach the best mode of the invention. The following claims specify the scope of the invention. Note that some aspects of the best mode may not fall within the scope of the invention as specified by the claims. Those skilled in the art will appreciate that the features described above can be combined in various ways to form multiple variations of the invention. As a result, the invention is not limited to the specific embodiments described above, but only by the following claims and their equivalents.

What is claimed is:

1. A method of operating an Amplicon Sequencing Analysis Pipeline (ASAP) system to characterize a genetic sample, the method comprising receiving assay configuration data to characterize the genetic sample, the method characterized by:
receiving the assay configuration data that individually associates reference sequences and genetic characteristics;
receiving amplicon sequencing data for the genetic sample;
processing the amplicon sequencing data and the reference sequences to identify ones of the reference sequences;
processing the identified ones of the reference sequences and the individual associations between the reference sequences and the genetic characteristics to identify ones of the genetic characteristics in the assay configuration data; and
transferring genetic data indicating the identified genetic characteristics for the genetic sample and indicating interpretation metrics for amplicon sequencing read depth and quality related to the identified genetic characteristics.

2. The method of claim 1 wherein:
receiving the assay configuration data further comprises receiving amplicon identity thresholds for the reference sequences;
processing the amplicon sequencing data and the reference sequences comprises processing the amplicon identity thresholds to determine amplicon identity between the amplicon sequencing data and the target amplicon sequences; and
transferring the genetic data comprises indicating the amplicon identity.

3. An Amplicon Sequencing Analysis Pipeline (ASAP) system to characterize a genetic sample comprising a user interface, a processing system, and a communication interface, the ASAP system characterized by:
the user interface configured to receive assay configuration data that individually associates reference sequences and genetic characteristics;
the processing system configured to process amplicon sequencing data and the reference sequences to identify ones of the reference sequences;
the processing system configured to process the identified ones of the reference sequences and the individual associations between the reference sequences and the genetic characteristics to identify ones of the genetic characteristics in the assay configuration data;
the processing system configured to generate genetic data indicating the identified genetic characteristics for the genetic sample and indicating interpretation metrics for amplicon sequencing read depth and quality related to the identified genetic characteristics; and
the communication interface configured to transfer the genetic data.

4. The ASAP system of claim 3 wherein:
the user interface is further configured to receive amplicon identity thresholds for the reference sequences;
the processing system is further configured to process the amplicon identity thresholds to determine amplicon identity between the amplicon sequencing data and the reference sequences; and
the processing system is further configured to transfer the genetic data indicating the amplicon identity.

5. An Amplicon Sequencing Analysis Pipeline (ASAP) computer apparatus to characterize a genetic sample, the ASAP computer apparatus comprising data processing circuitry and at least one or more non-transitory computer-readable storage medium, the computer apparatus characterized by:
assay software configured to direct the data processing circuitry to process amplicon sequencing data for the genetic sample and assay configuration data that individually associates reference sequences and genetic characteristics to identify ones of the reference sequences;
the assay software configured to direct the data processing circuitry to process the identified ones of the reference sequences and the individual associations between the reference sequences and the genetic characteristics to identify ones of the genetic characteristics in the assay configuration data;
alignment software configured to direct the data processing circuitry to generate genetic data indicating the identified genetic characteristics for the genetic sample and indicating interpretation metrics for amplicon sequencing read depth and quality related to the identified genetic characteristics; and
the at least one non-transitory computer-readable storage medium storing the assay software and the alignment software.

6. The ASAP computer apparatus of claim 5 wherein:
the assay software is further configured to direct the data processing circuitry to receive amplicon identity thresholds for the reference sequences; and
the alignment software is further configured to direct the data processing circuitry to process the amplicon identity thresholds to determine amplicon identity between the amplicon sequencing data and the reference sequences and to generate the genetic data indicating the amplicon identity.

\* \* \* \* \*